United States Patent [19]

Kanayama et al.

[11] Patent Number: 4,579,957
[45] Date of Patent: Apr. 1, 1986

[54] PROCESS FOR PRODUCING POLYMALEIMIDE

[75] Inventors: Kaoru Kanayama; Yoshinobu Ohnuma, both of Ibaraki, Japan

[73] Assignee: Mitsubishi Petrochemical Co., Ltd., Tokyo, Japan

[21] Appl. No.: 736,531

[22] Filed: May 21, 1985

Related U.S. Application Data

[63] Continuation of Ser. No. 513,519, Jul. 13, 1983, abandoned.

[30] Foreign Application Priority Data

Jul. 13, 1982 [JP] Japan ................. 57-121465

[51] Int. Cl.$^4$ .............................. C07D 403/14
[52] U.S. Cl. .................... 548/421; 526/262
[58] Field of Search ............. 548/521; 526/262

[56] References Cited

U.S. PATENT DOCUMENTS

| | | | |
|---|---|---|---|
| 4,046,777 | 9/1977 | Müller et al. | 548/522 |
| 4,113,737 | 9/1978 | Balme et al. | 546/256 X |
| 4,130,564 | 12/1978 | Haug et al. | 548/522 |
| 4,131,632 | 12/1978 | Suzuki et al. | 525/510 |
| 4,138,406 | 2/1979 | Balasfalvy | 548/522 |
| 4,212,959 | 7/1980 | Fukami et al. | 525/422 |
| 4,393,177 | 7/1983 | Ishii et al. | 525/422 |
| 4,401,777 | 8/1983 | Tsuboi et al. | 524/108 |

Primary Examiner—Donald G. Daus
Assistant Examiner—William A. Teoli, Jr.
Attorney, Agent, or Firm—Sughrue, Mion, Zinn, Macpeak and Seas

[57] ABSTRACT

A process for producing a polymaleimide which comprises reacting an aromatic dialdehyde with 2 to 60 moles, per mole of the aromatic dialdehyde, of aromatic amine represented by the formula (I):

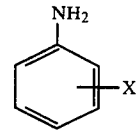

wherein X is a hydrogen atom, a halogen atom or an alkyl or alkoxy group each having 1 to 4 carbon atoms to obtain a polyamine, reacting the polyamine with maleic anhydride to obtain a polyamide acid, and dehydration-cyclizing the polyamide acid to obtain a polymaleimide.

4 Claims, 4 Drawing Figures

PROCESS FOR PRODUCING POLYMALEIMIDE

This is a continuation of application Ser. No. 513,519, filed July 13, 1983, now abandoned.

FIELD OF THE INVENTION

The present invention relates to a process for producing a novel polymaleimide having excellent curing properties. The polymaleimide produced by the process of this invention is soluble in common solvents such as methyl isobutyl ketone, methyl ethyl ketone, and chloroform, and is useful as a resin for prepreg.

BACKGROUND OF THE INVENTION

In view of the recent trend to sophistication and miniaturization of machines and equipment in the electric and electronic areas and aircraft and vehicles, a new material which has an excellent heat resistance is demanded. Heretofore, epoxy resins, maleimide resins, and polyimide resins were used in the field where the heat resistance is required. Epoxy resins, however, are not necessarily satisfactory in heat resistance and curing rate, although those have excellent electrical properties. Also, polyimide resins are insoluble and infusible and therefore difficult to mold, although those have an excellent heat resistance.

The polymaleimide represented by N,N'-4,4'-diphenylmethane bismaleimide has a high thermal stability, but has the disadvantage that it has a slow curing rate and requires heating at a high temperature for a long period of time for complete curing. This invention has been attained to improve the curing of polymaleimide.

SUMMARY OF THE INVENTION

Accordingly, an object of this invention is to provide a process for producing a polymaleimide which comprises reacting an aromatic dialdehyde with 2 to 60 moles, per mole of the aromatic dialdehyde, of aromatic amine represented by the formula (I):

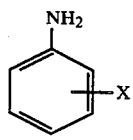

(I)

wherein X is a hydrogen atom, a halogen atom or an alkyl or alkoxy group having 1 to 4 carbon atoms, to obtain a polyamine, reacting the resulting polyamine with maleic anhydride to obtain a polyamide acid, and then dehydrationcyclizing the resulting polyamide acid to obtain a polymaleimide.

DETAILED DESCRIPTION OF THE INVENTION

Figure 1:
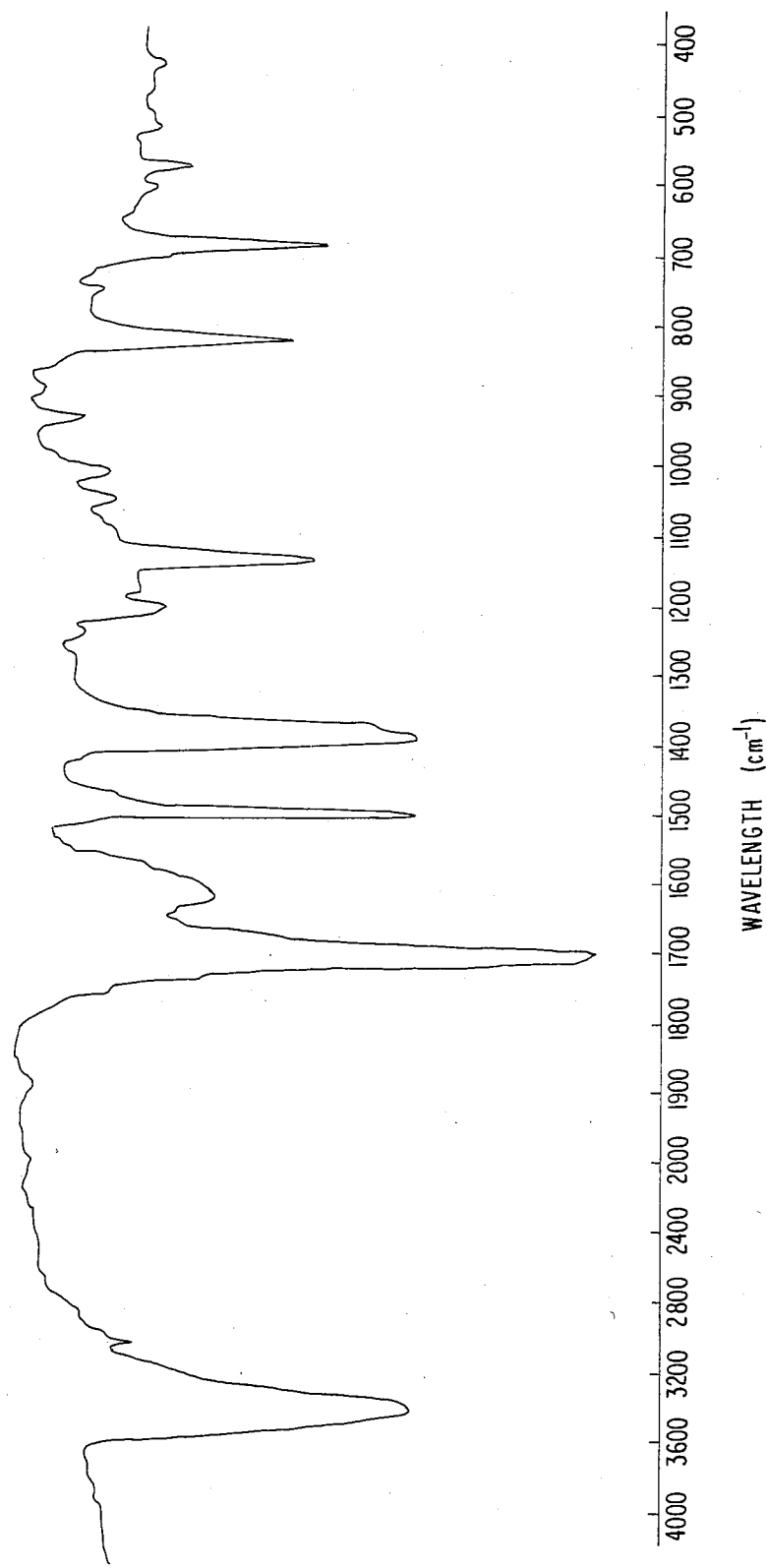
FIG. 1 and FIG. 3 are infrared absorption spectra of polymaleimides obtained in Examples 1 and 2 of this invention, respectively.

The aromatic dialdehyde used for producing the polyamine is a compound represented by the formula (II).

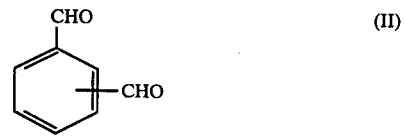

(II)

Preferred examples of the compound include 1,2-benzene dialdehyde, 1,3-benzene dialdehyde, and 1,4-benzene dialdehyde. Those compounds may have substituents such as halogen atoms and alkyl groups. The aromatic aldehyde may be used alone or mixtures thereof.

Examples of the aromatic amine include aniline, o-toluidine, m-toluidine, p-toluidine, o-ethylaniline, o-isopropylaniline, p-butylaniline, o-anisidine, o-phenetidine, chloroanilines, bromoanilines, etc.

The reaction of the aromatic dialdehyde and the aromatic amine is conducted in the presence of an acid catalyst such as mineral acids (e.g., hydrochloric acid or sulfuric acid); organic acid (e.g., p-toluenesulfonic acid); and organic acid salts, at 40° to 150° C. for 1 to 10 hours. The aromatic dialdehyde/aromatic amine molar ratio is 1:2 to 1:60, preferably 1:5 to 1:50.

After the reaction, the reaction mixture is neutralized with an alkali represented by sodium hydroxide, and washed with water, and the excess aromatic amine is then removed under reduced pressure to obtain a polyamine.

The thus obtained polyamine is a solid at room temperature, and contains at least 60 wt% of the compound having the structure represented by the formula (III).

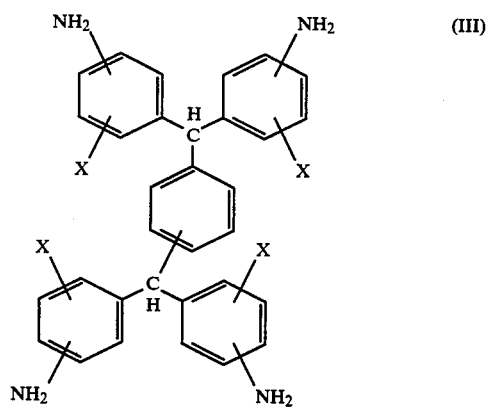

(III)

wherein X's, which may be the same or different, each is a hydrogen atom, halogen atom or an alkyl or alkoxy group each having 1 to 4 carbon atoms.

The polyamine further contains less than 40 wt% of the compound having 7 or more NH$_2$ groups represented by the formula (IV), which is formed by the condensation reaction of the polyamine of the formula (III) with the aromatic aldehyde and also the reaction of the resulting compound with the aromatic amine.

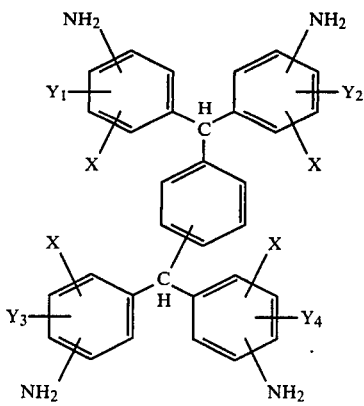

(IV)

wherein X's are the same as defined in formula (III); $Y_1$, $Y_2$, $Y_3$ and $Y_4$, which may be the same or different, each is a hydrogen atom or a group of the formula:

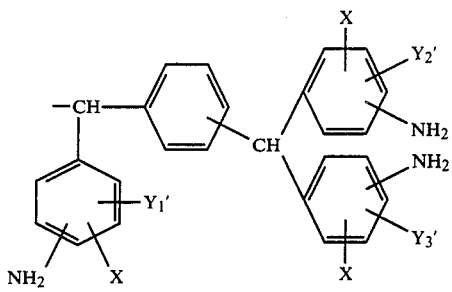

wherein $Y_1'$, $Y_2'$ and $Y_3'$, which may be the same or different, each is a hydrogen atom or a group of the formula:

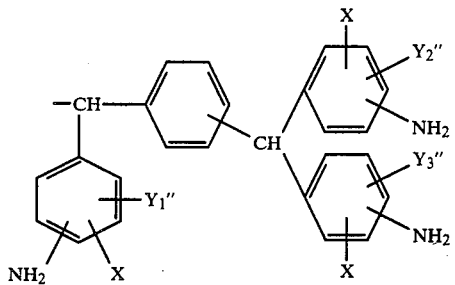

wherein $Y_1''$, $Y_2''$ and $Y_3''$, which may be the same or different, each is a hydrogen atom or a group of the formula:

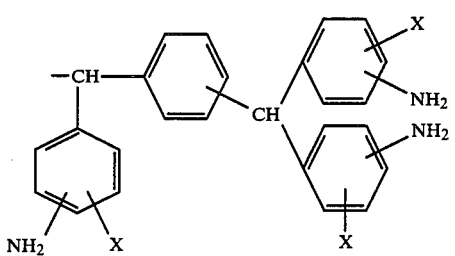

wherein X's are the same as defined above.

The presence of polyamines having 7 or more $NH_2$ groups was confirmed by gel permeation chromatography.

This polyamine is reacted with maleic anhydride to obtain a polyamide acid. Maleic anhydride dissolved in a proper organic solvent is added in an amount of at least one mole per one equivalent amount of amino group in the polyamine. The reaction is conducted at 0° to 40° C. for 0.5 to 2 hours.

Examples of the organic solvent include N,N'-dimethylformamide, acetone, methyl ethyl ketone, dioxane, N,N'-dimethylacetamide, dimethylsulfoxide, and N-methylpyrrolidone.

The thus obtained polyamide acid is dehydrated and cyclized by adding acetic anhydride as a dehydrating agent and, if necessary, a catalyst. This reaction is conducted at 20° to 80° C. for 1 to 5 hours. Thus, the desired polymaleimide is obtained.

Examples of the catalyst include cobalt acetate, nickel acetate, triethylamine, tri-n-propylamine, and tri-n-butylamine.

The polymaleimide thus produced is purified by water washing and drying.

The polymaleimide is usually a mixture, 60 wt% of which being the compounds represented by the formula (V).

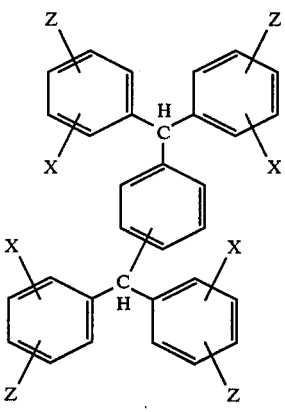

wherein X's, which may be the same or different, each is a hydrogen atom, a halogen atom or an alkyl or alkoxy group each having 1 to 4 carbon atoms, and Z is a group represented by the formula:

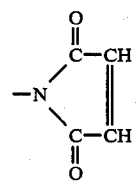

The polymaleimide also contains the compounds represented by the formula (VI):

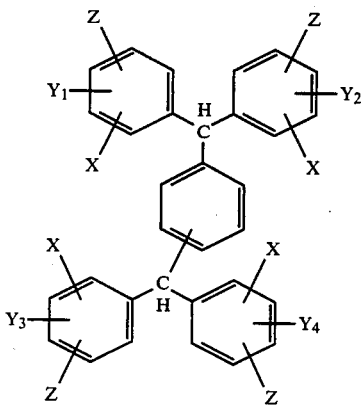

wherein X and Z are the same as defined in formula (V); and $Y_1$, $Y_2$, $Y_3$ and $Y_4$, which may be the same or different, each is a hydrogen atom or a group of the formula:

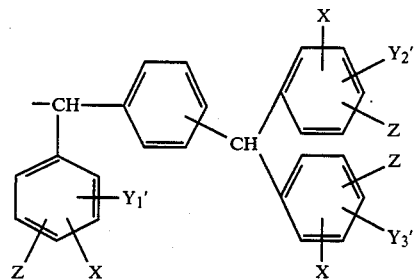

wherein $Y_1'$, $Y_2'$ and $Y_3'$, which may be the same or different, each is a hydrogen atom or a group of the formula:

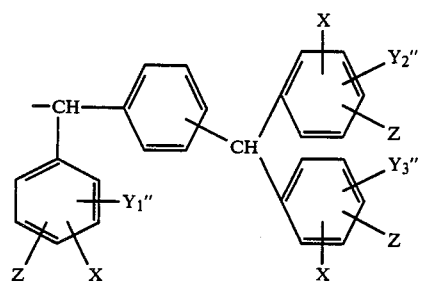

wherein $Y_1''$, $Y_2''$ and $Y_3''$, which may be the same or different, each is a hydrogen atom or a group of the formula:

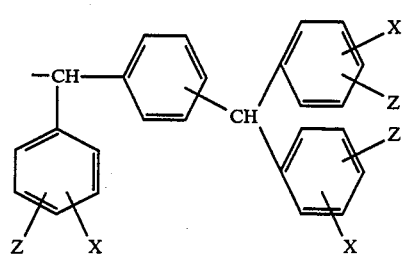

wherein X and Z are the same as defined above.

The polymaleimide obtained according to the process of this invention undergoes a radical polymerization to form a polymer.

When heated in the presence of an amine as a curing agent, the polymaleimide undergoes addition polymerization, in addition to the above-mentioned radical polymerization, to obtain a cured product having an excellent heat resistance.

The amine used as a curing agent includes, for example, aniline, toluidine, xylidine, vinylaniline, iropropenylaniline, phenylenediamine, diaminocyclohexane, ethylenediamine, trimethylenediamine, tetramethylenediamine, hexamethylenediamine, 4,7-dioxadecane-1,10-diamine, 4,4'-diaminodicyclohexylmethane, m-xylylenediamine, p-xylylenediamine, 2,4-diaminotoluene, 2,6-diaminotoluene, 4,4-diaminodiphenylmethane, 3,4'-diaminodiphenylmethane, bis(3-chloro-4-aminophenyl)methane, 2,2-bis(4-aminophenyl)propane, 4,4'-diaminophenylether, 4,4'-diaminodiphenylsulfide, 4,4'-diaminodiphenylsulfone-1,5-diaminonaphthalene, bis(4-aminophenyl)methylphosfinoxide, 4-methyl-2,4-bis(4'-aminophenyl)pentene-1,5-amino-1-(4'-aminophenyl)-1,3,3-trimethylindan, tris(4-aminophenyl)phosphate, 2,4-bis(4'-aminobenzyl)aniline, 2,2-bis[4-(4''-aminophenoxy)phenyl]propane, and dimer and polymer of vinylaniline, and polyamines of aniline and formaldehyde.

The amine is used in an amount of 5 to 100 parts by weight per 100 parts by weight of polymaleimide.

The polymaleimide produced according to the process of this invention is advantageous over the conventional polymaleimide in having a faster curing rate.

Therefore, it is possible to increase the curing rate of the conventional polymaleimide by adding the polymaleimide of this invention in an amount of 20 to 95 wt% based on the weight of the conventional polymaleimide. Examples of the polymaleimide include, N,N'-ethylenebismaleimide, N,N'-hexamethylenebismaleimide, N-phenylmaleimide, N,N'-m-phenylenemaleimide, N,N'-p-phenylenebismaleimide, N,N'-4,4'-diphenylmethanebismaleimide, N,N'-4,4'-diphenyletherbismaleimide, N,N'-methylenebis(3-chloro-p-phenylene)bismaleimide, N,N'-4,4'-diphenylsulfonbismaleimide, N,N'-α,α'-4,4'-dimethylenecyclohexanebismaleimide, N,N'-m-xylenebismaleimide, N,N'-4,4'-diphenylcyclohexanebismaleimide, and polymaleimides prepared from anilin-formaldehyde condensate and maleic anhydride.

It is also possible to improve the heat resistance of epoxy resins by adding the polymaleimide of this invention to a polyepoxy compound in an amount of 5 to 100 wt%, preferably 10 to 50 wt%, based on the weight of the polyepoxy compound.

Examples of the polyepoxy compound include the following materials:

(i) Glycidyl ether of bisphenol A, such as Eikote 827, 828, 834, 864, 1001, 1004, 1007 and 1031 made by Yuka-Shell Epoxy Co., Ltd.; Araldite GY250 and GY6099 made by Ciba Co., Ltd.; ERL2774 made by Union Carbide Corp.; and DER332, DER331 and DER661 made by Dow Chemical Co., Ltd.

(ii) Epoxyphenol novolak, such as Epikote 152 and 154 made by Yuka-Shell Epoxy Co., Ltd.; DEN438 and DEN448 made by Dow Chemical Co., Ltd.; and Araldite EPN138 and EPN1139 made by Ciba Co., Ltd.

(iii) Epoxycresol novolak, such as Araldite ECN1235, ECN1273 and ECN1280 made by Ciba Co., Ltd.

(iv) Glycidyl ether of bisphenol F, such as Epikote 807 made by Yuka-Shell Co., Ltd.

In addition, examples of the polyepoxy compound include epoxy resins obtained from phthalic acid or hexahydrophthalic acid and epichlorohydrin, epoxy resins obtained from parahydroxybenzoic acid and epichlorohydrin, epoxy resins obtained from an aromatic amine such as toluidine and aniline and epichlorohydrin; vinylcyclohexenedioxide, 1,4-butanediolglycidyl ether, and 1,6-hexanediolglycidyl ether. Of those materials, epoxy resins which are liquid at 20° C. and have an epoxy equivalent of 160 to 200 are preferred in view of the fact that they are easy to mix with the polymaleimide, filler and glass fiber.

The polymaleimide produced according to the process of this invention may contain a curing catalyst and promotor, and various additives such as filler, extender, pigment, flame retardant and flexibilizer, as required.

The incorporation of various additives and compounds can be accomplished by melt mixing, rolling, kneading, solution mixing or dry blending.

The invention is described in more detail by reference to the following examples. Unless otherwise indicated, all percents, parts, ratios and the like are by weight.

PREPARATION OF POLYAMINE

Preparation Example 1

Into a three-necked flask equipped with a thermometer, condenser and stirrer were charged 30 g (0.244 mol) of 1,3-benzenedialdehyde, 166.6 g (1.79 mol) of aniline, and 6.8 g of concentrated hydrochloric acid. The reaction was carried out for 5 hours under water reflux (at 107° C.).

After completion of the reaction, 20 g of 20% aqueous solution of sodium hydroxide was added, and the reactants were stirred for 5 minutes for neutralization. Then, 500 g of methyl isobutyl ketone was added to dissolve the separated product. The solution was washed three times with 300 g of pure water to remove sodium chloride formed as a by-product and excess sodium hydroxide.

The solution was then heated to 80° to 180° C. under vacuum (100 to 1 mmHg) to completely remove methyl isobutyl ketone and unreacted aniline. The residue was washed at 180° C. and then cooled to obtain 101.1 g of orangy transparent polyamine compound mixture containing 77% of polyamine represented by the following formula:

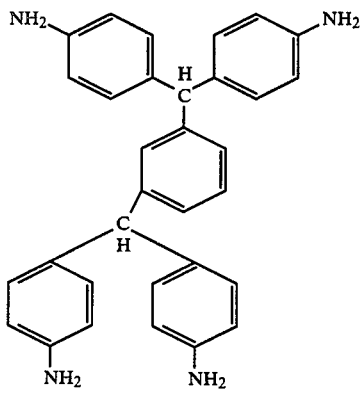

This polyamine was found to have a softening point of 115° to 121° C. (as measured by capillary method) and a neutralization equivalent of 118.

Preparation Example 2

The same reaction as in Preparation Example 1 was carried out, except that the reactants were replaced by 30 g (0.224 mol) of 1,4-benzenedialdehyde, 95.9 g (0.895 mol) of o-toluidine, and 83.3 g (0.895 mol) of aniline. Thus, 111.9 g of reddish transparent solid polyamine was obtained.

This polyamine was found to have a softening point of 122° to 128° C. and a neutralization equivalent of 126.

Incidentally, this polyamine was found to contain 82% of 5-nucleus compound represented by the formula (III).

Preparation Examples 3 to 11

The same reaction as in Preparation Example 1 was carried out, except that the aldehyde and amine were replaced by those as shown in Table 1. The resulting polyamines are also shown in Table 1.

TABLE 1

| Preparation Example No. | Reactants Benzenedialdehyde | Amine | Neutralization Equivalent of Polyamine |
|---|---|---|---|
| 3 | 1,4-substituted | o-ethylaniline | 148 |
| 4 | 1,4-substituted | m-anisidine | 149 |
| 5 | 1,4-substituted | chloroaniline | 154 |
| 6 | 1,3-substituted | m-toluidine | 133 |
| 7 | 1,3-substituted | bromoaniline | 201 |
| 8 | 1,3-substituted | o-toluidine | 132 |
| 9 | 1,2-substituted | p-butylaniline | 177 |
| 10 | 1,2-substituted | aniline | 119 |
| 11 | 1,2-substituted | phenetidine | 162 |

Neutralization equivalent was determined by titration with perchloric acid.

EXAMPLE 1

Into a 500 ml four-necked flask equipped with a thermometer, condenser, dropping funnel and stirrer were charged 39.3 g of maleic anhydride and 78.5 g of N,N'-dimethylformamide to dissolve maleic anhydride by stirring.

Then, 47.2 g of polyamine prepared in Preparation Example 1, which had been dissolved in 118 g of N,N'-dimethylformamide, was added dropwise while keeping the temperature of the flask at 20° to 30° C. Stirring was continued at the same temperature for 30 minutes.

To this flask were added 0.4 g of nickel acetate, 10 ml of triethylamine, and 61.3 g of acetic anhydride. The dehydration-cyclization reaction was carried out by stirring at 60° C. for 3 hours.

After completion of the reaction, the reaction product was thrown into a large amount of water to separate out the crystals of polymaleimide. The crystals were filtered out and washed with water and dried. Thus, 83.9 g (yield: 97%) of slightly yellowish polymaleimide was obtained.

Figure 2:
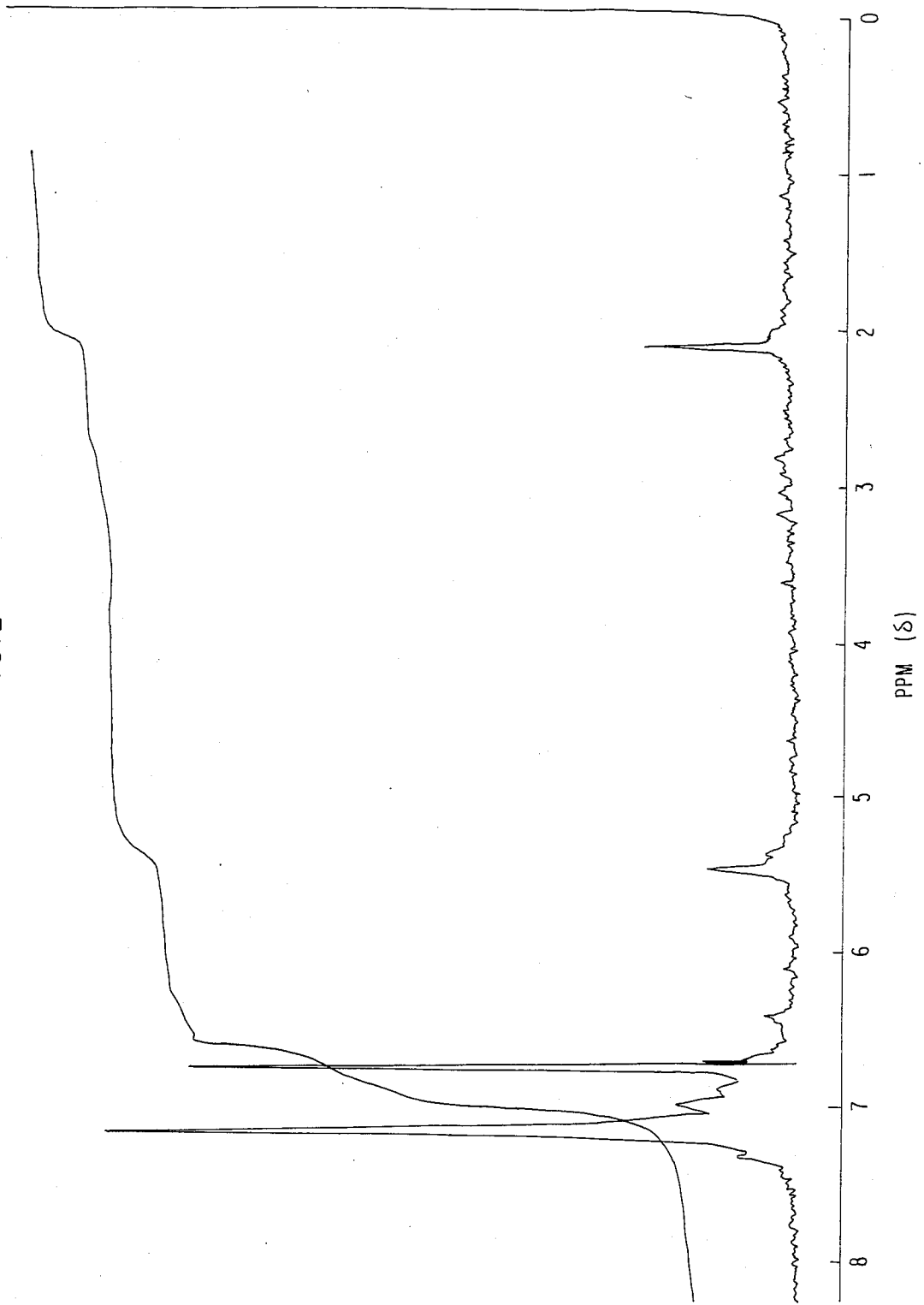
FIG. 2 and FIG. 4 are NMR spectra of polymaleimides obtained in Examples 1 and 2 of this invention, respectively.

This polymaleimide was found to have a softening point of 166° to 180° C. (measured by capillary method). The infrared absorption spectrum and NMR spectrum of this polymaleimide are shown in FIG. 1 and FIG. 2, respectively.

EXAMPLES 2 TO 11

Example 1 was repeated except that the polyamine was replaced by the ones prepared in Preparation Examples 2 to 11 and the amount of N,N'-dimethylformamide was changed as shown in Table 1 to obtain polymaleimides in yield of 95 to 97%. The properties of the polymaleimide are shown in Table 2.

Figure 3:
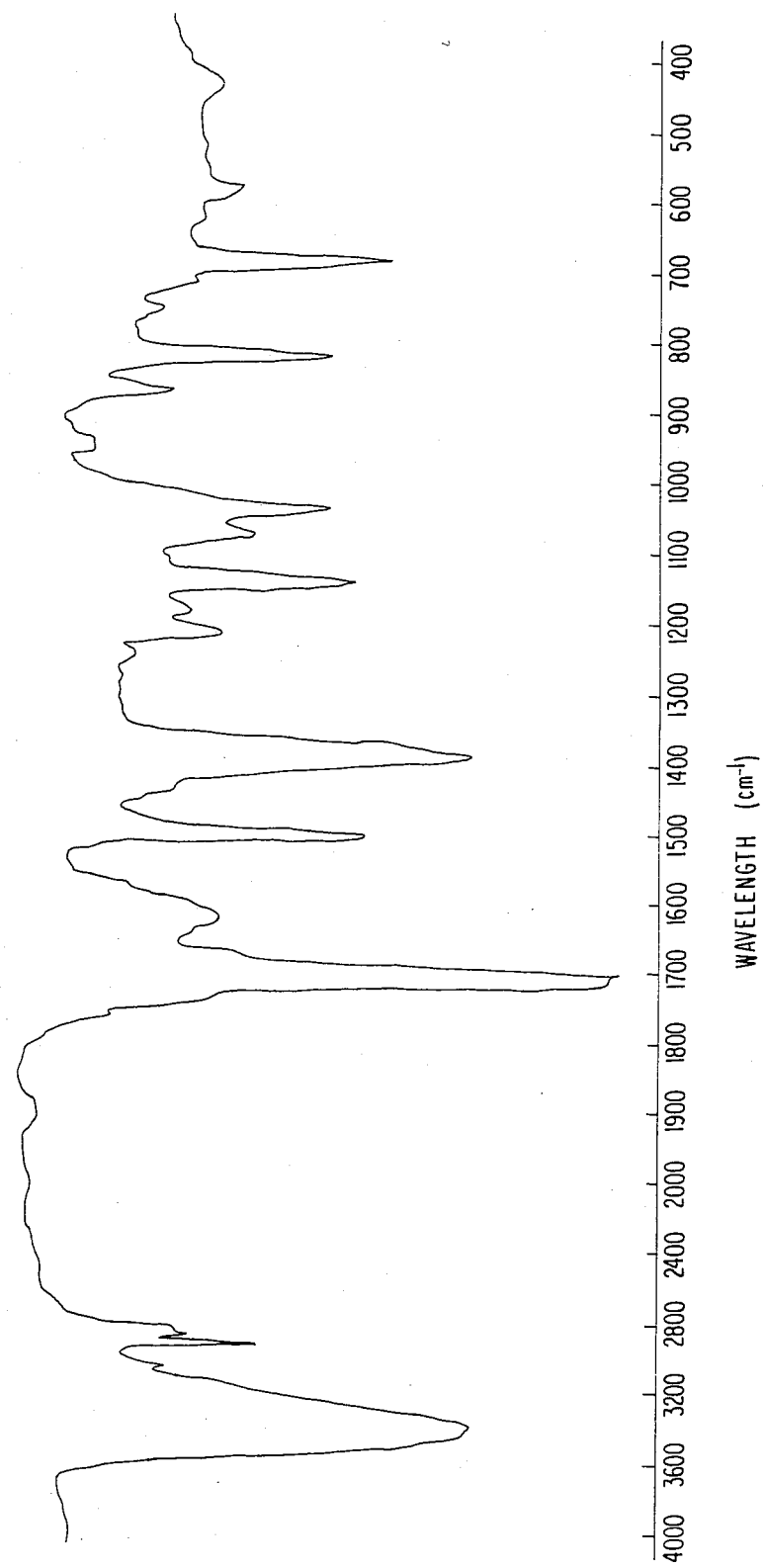
Figure 4:
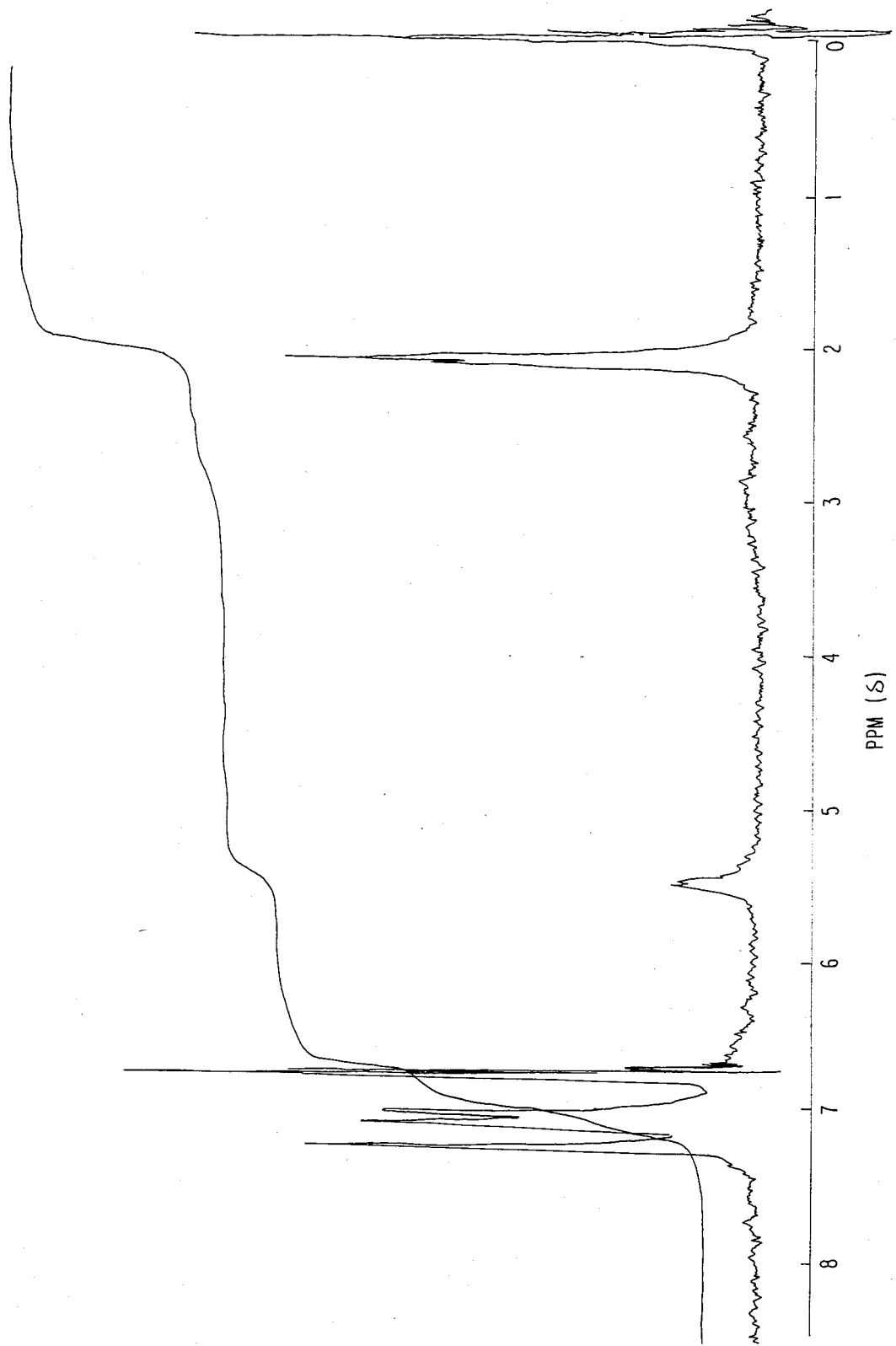

The infrared absorption spectrum and NMR spectrum of the polymaleimide obtained in Example 2 are shown in FIG. 3 and FIG. 4, respectively.

TABLE 2

| Example No. | Polyamine Preparation Example | Amount Used (g) | Amount of N,N'—Dimethyl-formamide Used (g) | Softening Point of Polymaleimide (°C.) |
|---|---|---|---|---|
| 1 | 1 | 47.2 | 118 | 168–180 |
| 2 | 2 | 50.4 | 126 | 178–190 |
| 3 | 3 | 59.2 | 148 | 142–148 |
| 4 | 4 | 59.6 | 149 | 155–165 |
| 5 | 5 | 61.6 | 154 | 189–198 |
| 6 | 6 | 53.2 | 133 | 163–172 |
| 7 | 7 | 80.4 | 201 | 190–200 |
| 8 | 8 | 52.8 | 132 | 165–173 |
| 9 | 9 | 70.8 | 177 | 125–140 |
| 10 | 10 | 47.6 | 119 | 145–155 |
| 11 | 11 | 64.8 | 162 | 128–138 |

PRODUCTION OF CURED PRODUCTS

Production Example 1

100 parts of a mixture prepared by heat dissolving 30 parts of polymaleimide prepared in Example 1 and 70 parts of glycidyl ether of bisphenol A ("Epikote 828", a product of Yuka-Shell Epoxy Co., Ltd.), 25 parts of 4,4'-diaminodiphenylmethane, and 200 parts of silica as a filler were kneaded using rolls at 70° to 90° C. for 20 minutes.

The resulting composition was crushed and the crushed powder was charged into a press metallic mold, compression molded at 200° C. under 100 kg/cm² for 10 minutes and cooled to 40° C. to obtain a molded product having a size of 12.7 cm long, 1.27 cm wide, and 0.64 cm high.

The physical properties of the molded product are shown in Table 3.

The molded product was then cured at 230° C. for 10 hours. The physical properties of the cured product are also shown in Table 3.

Production Example 2

Production Example 1 was repeated except that the polymaleimide was replaced by the one obtained in Example 2.

Production Example 3 (For Comparison)

Production Example 1 was repeated except that the polymaleimide was replaced by commercially available N,N'-4,4'-diphenylmethanebismaleimide.

Production Example 4 (For Reference)

A resin composition was prepared by roll milling 100 parts of glycidyl ether of bisphenol A ("Epikote 828"), 26 parts of 4,4'-diaminodiphenylmethane, and 200 parts of silica at 80° C. for 20 minutes.

The resulting crushed powder was molded and the molded product was cured in the same manner as in Production Example 1.

The physical properties of the molded product and cured product obtained in Production Examples 2 to 4 are shown in Table 3.

The cured products were kept in an oven at 230° C. for 1500 hours and 3500 hours, and the retention of flexural strength thereof was measured at 20° C. The results are also shown in Table 3.

TABLE 3

| | Production Example No. | | | |
|---|---|---|---|---|
| | 1 | 2 | 3 | 4 |
| Molded Product | | | | |
| Molding Conditions | 200° C., 100 kg/cm², 10 minutes | | | |
| Heat Distortion Temperature (° C.)* | 165 | 167 | 139 | 168 |
| Flexural Strength at 23° C. (kg/mm²)** | 10.2 | 10.1 | 10.1 | 10.0 |
| Flexural Modulus of Elasticity at 23° C. (kg/mm²)** | 1100 | 1100 | 1080 | 890 |
| Weight Loss on Heating (%) (230° C., 500 hours) | 2.3 | 2.2 | 2.6 | 2.9 |
| Cured Product | | | | |
| Curing Conditions | 230° C., 10 hours | | | |
| Heat Distortion Temperature (°C.) | 248 | 251 | 198 | 171 |
| Flexural Strength at 23° C. (kg/mm²)** | 10.9 | 11.0 | 10.9 | 10.3 |
| Flexural Modulus of Elasticity at 23° C. (kg/mm²)** | 1250 | 1260 | 1160 | 980 |
| Heat Resistance Test: Retention of Flexural Strength (%) | | | | |
| 230° C. × 1500 hours | 89 | 87 | 53 | 23 |
| 230° C. × 3500 hours | 80 | 79 | 48 | broken |

*ASTM D-648
**ASTMD-790

Production Example 5

The molding conditions in Production Example 3 were changed to 200° C., 100 kg/cm², and 60 minutes. The heat distortion temperature of the molded product was 165° C. The molded product was cured at 230° C. for 50 hours. The heat distortion temperature of the cured product was 207° C.

While the invention has been described in detail and with reference to specific embodiments thereof, it will be apparent to one skilled in the art that various changes and modifications can be made therein without departing from the spirit and scope thereof.

What is claimed is:

1. A polymaleimide prepared by a process which comprises reacting an aromatic dialdehyde of the formula (II):

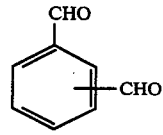

which may be substituted with one or more halogen atoms and alkyl groups; with 2 to 60 moles of an aromatic amine per mole of the aromatic dialdehyde to obtain a polyamine:
wherein said aromatic amine is represented by the formula (I):

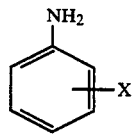

wherein X is a hydrogen atom, a halogen atom or an alkyl or alkoxy group each having 1 to 4 carbon atoms; and reacting said polyamine with maleic anhydride to obtain a polyamide acid to obtain a polymaleimide.

2. A polymaleimide prepared by the process of claim 1, wherein the polymaleimide is represented by the formula:

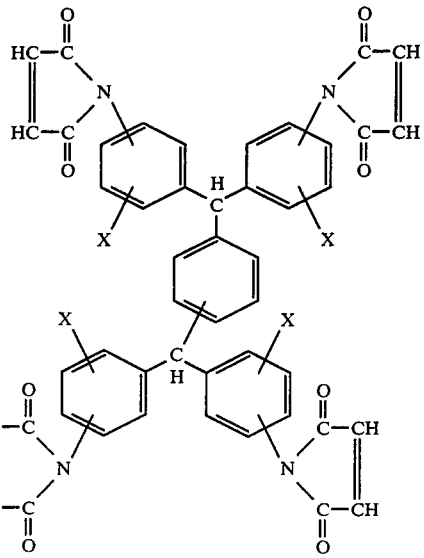

where X's, which may be the same or different, each is a hydrogen, a halogen atom or an alkyl or alkoxy group each having 1 to 4 carbon atoms.

3. A polymaleimide prepared by the process claimed in claim 1, wherein the aromatic amine is a compound selected from the group consisting of aniline, toluidine, chloroaniline, bromoaniline, ethylaniline, butylaniline, anisidine, and phenitidine.

4. A polymaleimide prepared by the process claimed in claim 1, wherein the aromatic dialdehyde is selected from the group consisting of 1,2-benzene dialdehyde, 1,3-benzene dialdehyde, and 1,4-benzene dialdehyde.

* * * * *